(12) United States Patent
Van Der Windt

(10) Patent No.: US 10,183,052 B2
(45) Date of Patent: Jan. 22, 2019

(54) MUTANT TOMATOES AND USE THEREOF FOR PREVENTING WEIGHT GAIN AND/OR TREATING OBESITY-RELATED CONDITIONS

(71) Applicant: GREEN4HEALTH B.V., Winschoten (NL)

(72) Inventor: Arie-Dirk Van Der Windt, Winschoten (NL)

(73) Assignee: Green4Health B.V. (NL)

( * ) Notice: Subject to any disclaimer, the term of this patent is extended or adjusted under 35 U.S.C. 154(b) by 72 days.

(21) Appl. No.: 15/357,756

(22) Filed: Nov. 21, 2016

(65) Prior Publication Data

US 2017/0065655 A1  Mar. 9, 2017

Related U.S. Application Data

(62) Division of application No. 14/421,663, filed on Feb. 13, 2015, now abandoned.

(51) Int. Cl.
| | |
|---|---|
| A61K 36/00 | (2006.01) |
| A61K 36/81 | (2006.01) |
| A61K 31/702 | (2006.01) |
| A61K 45/06 | (2006.01) |
| A23L 33/105 | (2016.01) |
| A23L 33/00 | (2016.01) |
| A23L 33/21 | (2016.01) |

(52) U.S. Cl.
CPC ............ *A61K 36/81* (2013.01); *A23L 33/105* (2016.08); *A23L 33/21* (2016.08); *A23L 33/30* (2016.08); *A61K 31/702* (2013.01); *A61K 45/06* (2013.01); *A61K 2236/15* (2013.01); *A61K 2236/17* (2013.01); *A61K 2236/33* (2013.01); *A61K 2236/333* (2013.01); *A61K 2236/51* (2013.01)

(58) Field of Classification Search
CPC .................................................. A61K 36/00
See application file for complete search history.

(56) References Cited

U.S. PATENT DOCUMENTS

2003/0129292 A1* 7/2003 Blaker .................... A23L 27/63
426/589

FOREIGN PATENT DOCUMENTS

| CN | 101 703 290 | 5/2010 |
| JP | 2011 184 411 | 9/2011 |
| WO | 2004 017 760 | 3/2004 |
| WO | 2007 031 291 | 3/2007 |
| WO | 2009 112 546 | 9/2009 |
| WO | 2010 042 865 | 4/2010 |

OTHER PUBLICATIONS

Ito, et al., "Why Does the Tomato with the Rin Mutation Fail to Ripen? The Molecular Function of MADS-Box Transcription Factor RIN that Controls Ripeness of Fruits," Kagaku to Seibutsu, 2009, vol. 47, No. 7, p. 465-472.
US Department of Agriculture, "Plant Inventory," 1969, No. 173, p. 6-11, https://naldc.nal.usda.gov/download/39200/PDF.
Kim, et al. "Identification of Tomato-derived Functional Ingredients Ameliorating Lipid Metabolism and Comparison of the Content thereof between Varieties," Abstract Proceedings of 65th Annual Meeting of Japan Society of Nutrition and Food Science, Apr. 2011, p. 171.
Shimizu, et al., "Lipid Metabolism and Enteral Environment Control," Rinshoeiyo, Sep. 2005, vol. 107, No. 3, p. 283-286.
JP Office Action Translation, JP Patent Application No. 2015-527416, dated Jul. 4, 2017.
PCT Publication with Search Report/Written Opinion, WO 2014 027886, dated Feb. 20, 2014.
Vrebalov, J., Ruezinsky, D., Padmanabhan, V., White, R., Medrano, D., Drake, R., Schuch, W., Giovannoni, J., "A MADS-Box Gene Necessary for Fruit Ripening at the Tomato Ripening-Inhibitor (Rin) Locus," www.sciencemag.org, Science, vol. 296, Apr. 12, 2002.
Choi, K.M., Lee, Y.S., Shin, D.M., Lee, S., Yeo, K.S., Lee, M.K., Lee, J.H., Kim, S.Y., Lee, Y.M., Hong, J.T., Yun, Y.P., Yoo, H.S., "Green Tomato Extract Attenuates High-Fat-Diet-Induced Obesity through Activation of the AMPK Pathway in C57BL/6 Mice," Journal of Nutritional Biochemistry 24, (2013), pp. 335-342.
Horiba, T., Nishimura, I., Nakai, Y., Abe, K., Sato, R., "Naringenin Chalcone Improves Adipocyte Functions by Enhancing Adiponectin Production," Molecular and Cellular Endocrinology 323, (2010), pp. 208-214.
Tainaka, T., Shimada, Y., Kuroyanagi, J., Zang, I., Oka, T., Nishimura, Y., Nishimura, N., Tanaka, T., "Transcriptome Analysis of Anti-Fatty Liver by Campari Tomato using a Zebrafish Diet-Induced Obesity Model," Nutrition and Metabolism 2011, 8:88.
Jones, M.M., Rice, M.S., "Anthocyanin Analysis in the Diageotropica Tomato Plant," Book of Abstracts, 217th ACS National Meeting, Anaheim, CA, Mar. 21-25, 1999, CHED-386, American Chemical Society, Washington, D.C. CODEN: 67GHA6.
Negi, S., Sukumar, P., Liu, X., Cohen, J.D., Muday, G.K., "Genetic Dissection of the Role of Ethylene in Regulating Auxin-Dependent Lateral and Adventitious Root Formation in Tomato," The Plant Journal: for Cell and Molecular Biology, vol. 61, No. 1, 2010, p. 3-15.

(Continued)

*Primary Examiner* — Qiuwen Mi
(74) *Attorney, Agent, or Firm* — Emerson Thomson Bennett, LLC; Daniel A. Thomson

(57) ABSTRACT

The invention relates to the use of tomatoes for inhibition, amelioration or prevention of adipogenesis mediated diseases such as obesity, lipid storage disease and hyperlipemia. Provided is a tomato plant, fruit, fragment or extract thereof for use in a method for preventing weight gain, and/or inhibiting, preventing or ameliorating a disease condition associated with adipogenesis in a mammal, wherein the tomato is a ripening-impaired mutant tomato, such as a ripening inhibitor (rin), nonripening (nor), and/or never ripe (Nr) gene mutant tomato. Also provided are anti-adipogenic extracts and compositions comprising the extract.

20 Claims, 1 Drawing Sheet

(56) References Cited

OTHER PUBLICATIONS

Sundberg, B., "Influence of Extraction Solvent (Buffer, Methanol, Acetone) and Time on the Quantification of Indole-3-Acetic Acid in Plants," Physiologia Planetarum, vol. 78, No. 2, 293-297, Copenhagen 1990.

Gross, K.C., "Fractionation and Partial Characterization of Cell Walls from Normal and Non-Ripening Mutant Tomato Fruit," Physiologia Planetarum, vol. 62, No. 1, 25-31, Copenhagen 1984.

* cited by examiner

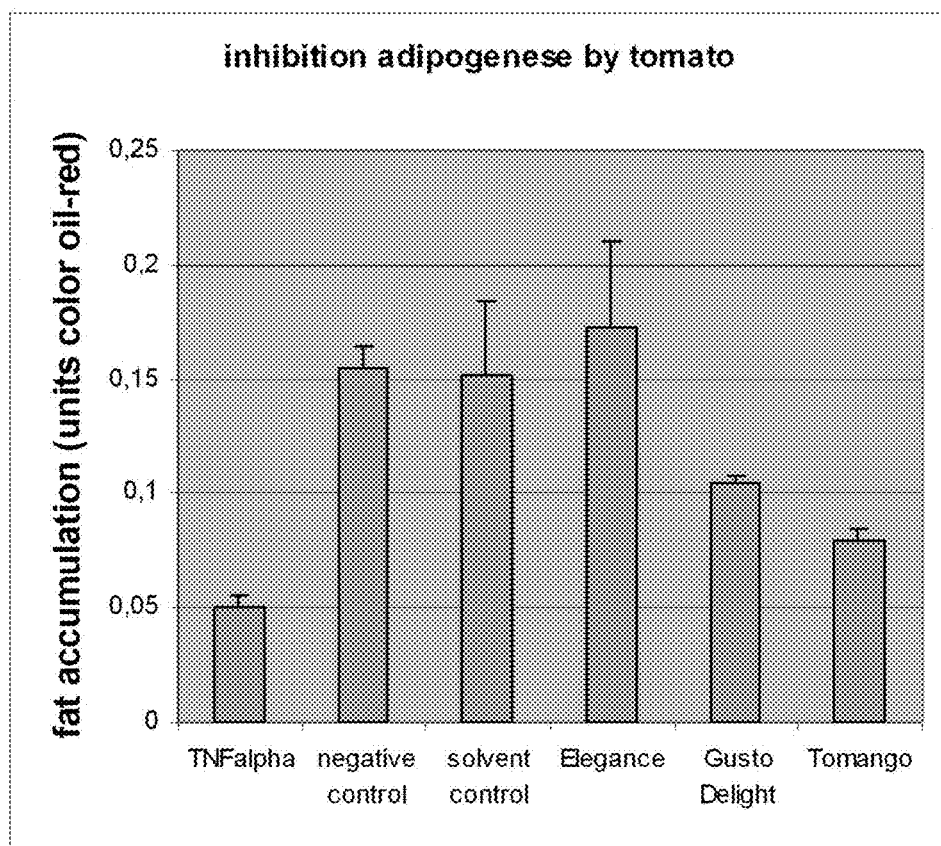

MUTANT TOMATOES AND USE THEREOF FOR PREVENTING WEIGHT GAIN AND/OR TREATING OBESITY-RELATED CONDITIONS

The invention relates to the use of tomatoes for preventing weight gain, and/or treating obesity-related conditions, such as obesity, lipid storage disease and hyperlipemia. The invention further relates to a method for treating or preventing adipogenesis involved diseases in mammals using the invented compositions.

Obesity is excess body weight for a particular age, sex and height as a consequence of imbalance between energy intake and energy expenditure. The primary cause of obesity is either due to overeating, inadequate exercise or eating disorder, some genetic disorders, underlying illness (e.g., hypothyroidism), certain medications, sedentary lifestyle, a high glycemic diet (i.e., a diet that consists of meals that give high post-prandial blood sugar) weight cycling (caused by repeated attempts to lose weight by dieting, eating disorders), stress and insufficient sleep.

Obesity is the culmination of many underlying mechanisms. Obesity is characterized as uncontrolled adipose tissue mass in the body and recognized as the fastest growing metabolic disorder in the world. An increase in adipose tissue mass can be the result of the production of new fat cells through the process of adipogenesis and/or the deposition of increased amounts of cytoplasmic triglyceride or lipid droplets per cell. Adipogenesis is the process of cell differentiation by which preadipocytes become adipocytes. In the adipogenesis process, proliferation of preadipocytes or precursor fat cells needs to be followed by the differentiation of these cells to the mature adipocyte phenotype. Increased lipid accumulation in the mature adipocyte cells is the most important feature of obesity disorder.

Fat is stored as triglycerides form in adipose tissue. The breakdown of this fat in fat cells into glycerol and fatty acids is known as lipolysis. During this process, free fatty acids are released into the bloodstream and circulate throughout the body. The hormones such as epinephrine, norepinephrine, glucagon and adrenocorticotropic hormone induce lipolysis. These hormones trigger 7TM receptors, which activate adenylate cyclase. This results in increased production of cAMP, which activates protein kinase A. Protein kinase A subsequently activates lipases found in adipose tissue.

Reducing the formation of new adipose tissue and formation of fat reserves through inhibition of differentiation of pre-adipocytes into mature adipocytes may be a good strategy to control adipogenesis mediated diseases, especially obesity. Modulation of adipogenesis and lipolysis in humans may thus lead to a reduction in the burden of obesity.

Low caloric diets with or without exercise can help with temporary weight loss; however, diet and exercise alone have not proven successful for long-term solutions in weight management. In addition, supplementation with drugs that suppress appetite, reduce food intake, reduce dietary fat absorption, increase energy expenditure and effect nutrient partitioning or metabolism have potential efficacy but they are unfortunately accompanied by adverse side effects (C. A. Haller and N. L. Benowitz., New England J. Medicine, 2000, 343, 1833-1838). The pharmaceutical drug, such as phentermine (Fastin, Adipex P), is prescribed for weight control but these have side effects like high blood pressure, headache, insomnia, irritability and nervousness. The other important drugs for weight control are Xenical (Roche Pharm. Co. Ltd., Swiss) and Reductil (Abbot Co. Ltd., USA), which cause gas generation, cramps, diarrhea and elevated blood pressure, common side effects. All these therapies are based on active ingredients that are of synthetic origin.

Effective anti-obese therapies with satisfactory efficacy and acceptable safety have been long overdue. More importantly, anti-obese agents of natural origin with proven safety are greatly needed to control the growing menace. Many herbal and natural products containing gymnema extract, garcinia extract, or carnitine, for example are known to prevent fat accumulation through the inhibition of fat absorption, enhancement of fat decomposition, and the enhancement of fat consumption by the body. It is particularly advantageous for inhibition, amelioration and prevention of obesity if an anti-obesity action can be imparted to a food product which is ordinarily ingested by a mammal, in particular a human being. Preferably, the anti-obese food product furthermore satisfies one or more of the following criteria: (i) it is of low caloric value, (ii) of natural origin (iii) non-transgenic (iv) easy to obtain (v) economically attractive.

The present inventors surprisingly observed that tomatoes which are impaired in ripening, e.g. the ripening-impaired mutants rin, nor, and Nr, have an anti-adipogenic effect. For example, fruits of tomatoes which carry the ripening inhibitor (rin) mutation were evaluated in an assay for adipocyte differentiation, the process in which a relatively unspecialized cell acquires specialized features of an adipocyte, an animal connective tissue cell specialized for the synthesis and storage of fat. It was surprisingly found that the extent of ripening impairment, e.g. the rin content, of a tomato is positively correlated with its capacity to inhibit lipid accumulation.

Accordingly, in one embodiment the invention provides a tomato plant, fruit, fragment or extract thereof for use in a method for preventing weight gain, and/or treating obesity-related conditions in a mammal, wherein the tomato is a ripening-impaired mutant. Ripening-impaired mutant tomatoes are known in the art. For example, the ripening-impaired mutant tomato carries the ripening inhibitor (rin), nonripening (nor), and/or never ripe (Nr) gene. It is also possible to generate novel ripening impaired mutants, for instance by exposing a tomato plant to gamma irradiation and selecting progeny thereof showing a ripening impaired phenotype.

The tomato (*Lycopersicon esculentum*) is a plant from the Solanaceae family (Solanaceae) native to America and cultivated all over the world for its edible fruit. Said fruit is a very coloured berry, with shades that typically change from yellowish to red, due to the presence of the lycopene and carotene pigments. It has a lightly acidic flavour, a diameter of 1 to 2 cm in the wild species, and is much bigger in the cultivated varieties. It is produced and consumed all over the world both fresh and processed in different ways, e.g. as a sauce, puree, juice, dehydrated or canned. The tomato is a food having a low quantity of calories. In fact, 100 grams of tomato only have 18 kcal. Most of its weight is water and carbohydrates are the second important constituent. It contains simple sugars that confer it a light sweet flavour and some organic acids that provide the characteristic acidic flavour. The tomato is an important source of certain minerals as potassium and magnesium. From its vitamin content, we can highlight the B1, B2, B5 and the vitamin C.

In one aspect, the mutant tomato carries the rin, nor and/or Nr gene. For example, the tomato is heterozygous for rin, nor and/or Nr. For example, the tomato is heterozygous or homozygous for nor. In one embodiment, the tomato has a nor content of at least 50%, preferably at least 65%, more preferably 70-100%. In another embodiment, the tomato is heterozygous or homozygous for Nr. In one embodiment, the tomato has a Nr content of at least 50%, preferably at least 65%, more preferably 70-100%.

In another embodiment, the tomato is homozygous for rin, nor and/or Nr. Rin and/or nor are preferred. For example, the invention is practised using a tomato having homozygous mutant rin genes, homozygous mutant nor genes or tomatoes heterozygous in both rin and nor genes.

In a preferred embodiment, the mutant tomato is a rin tomato since these can develop into fruits that are acceptable for human consumption. However, nonripening (nor), and/or never ripe (Nr) tomato plants are also suitably used, in particular in a processed form such as a fruit or root extract.

The ripening inhibitor gene (rin) is a semi-dominant tomato gene which was first described in 1968 by Robinson and Tomes, "Ripening Inhibitor: A Gene with Multiple Effects on Ripening." Rpt. Tomato Genetics Cooperative 18:36-37. The rin gene is available from several sources, including the C. M. Rick Tomato Genetic Resource Center (TGRC) at the University of California, Davis. The rin gene is described in the literature, e.g., in Davies et al. mentioned above.

Tomato plants harboring the rin mutation yield fruits that fail to ripen. Tissue softening and pigment synthesis which occur in normal tomato fruits are inhibited in fruits of rin tomato mutants (Davies et al. 1981, "The Constituents of Tomato Fruit—The Influence of Environment, Nutrition and Gene Type," CRC Critical Reviews in Food Science and Nutrition, 15:205-280), indicates that the deleterious effects of ripening inhibitor genes in the heterozygous state may possibly be overcome by incorporating genes which will enhance color, such as high pigment and crimson.

Additionally, rin plants display enlarged sepals and loss of inflorescence determinacy. Positional cloning of the rin locus revealed two tandem MADS-box genes (LeMADS-RIN and LeMADS-MC), whose expression patterns suggested roles in fruit ripening and sepal development, respectively. The rin mutation alters expression of both genes. Gene repression and mutant complementation demonstrate that LeMADS-RIN regulates ripening, whereas LeMADS-MC affects sepal development and inflorescence determinacy. LeMADS-RIN demonstrates an agriculturally important function of plant MADS-box genes and provides molecular insight into nonhormonal (developmental) regulation of ripening (Vrebalov et al. Science 12 Apr. 2002: Vol. 296 no. 5566 pp. 343-346).

U.S. Pat. No. 4,843,186 relates to a heterozygous tomato plant resulting from crossing a male parent containing the Rin/Rin gene with a female parent, said tomato plant having a rin gene from the male parent as a heterozygote and having the characteristics of a very firm fruit with excellent tomato-like taste having a shelf like of at least two weeks, without substantially deteriorating taste or firmness, and developing a full red color.

US 2003/0134026 discloses homozygous rin and/or nor tomatoes, or tomatoes heterozygous in both rin and nor are used to prepare a tomato paste, juice or sauce having good viscosity as well as good color.

US2003/0129292 discloses the use of homozygous rin and/or nor and/or alc tomatoes, or tomatoes heterozygous in both rin and nor and/or alc to prepare a tomato paste, juice or sauce having good viscosity as well as good color.

WO2004/017760 relates to a processed tomato product, comprising at least 10% tomatoes which are homozygous for rin, homozygous for nor, homozygous for Nr, homozygous for a/c, heterozygous for combinations of two of the rin, nor, Nr or alc genes, or combinations thereof.

Horiba et al. (Mol Cell Endocrinol. 2010 Jul. 29; 323(2): 208-14) reported that naringenin chalcone is a potent tomato flavenoid found in tomato peel that improves adipocyte metabolic functions and exerts insulin-sensitizing effects by activating an adiponectin-related pathway. No association between the rin gene and naringenin chalcone content is known. Moreover, the present inventors found that the anti-adipogenic capacity of rin tomatoes was found not to be confined to the peel.

Thus, the prior art fails to disclose or suggest an anti-adipogenic or lipid accumulation inhibition activity of a ripening-impaired mutant tomato, extracts or purified fractions thereof. More specifically, its application in the prevention or suppression of adipogenesis mediated disorders was not encompassed by the literature.

As used herein, a ripening inhibitor (rin) mutant tomato refers to a *Lycopersicon esculentum* expressing the mutant ripening inhibitor (rin) tomato gene, thus encompassing any variety in the spectrum ranging from heterozygous rin to homozygous rin tomatoes. In one embodiment, the tomato is heterozygous for rin. In another embodiment, the tomato is a homozygous rin tomato. Using tissue culture techniques, the present inventors succeeded in generating tomato varieties having a rin content from between 50 to 100%.

As used herein, the term "rin content" is defined as the amount of the tomato rin mRNA relative to the arbitrary amount of 100% rin in a rin/rin homozygous tomato. The rin content of a rin heterozygote is 50%. The rin content of a RIN homozygote is 0%.

The rin content is suitably determined by methods known in the art based on the known sequence of the rin gene. For example, standard PCR methodology can be used based on a set of primers designed to specifically detect the rin mutation. Quantitative real-time PCR (RT-PCR) is preferred. RT-PCR is currently the standard method for accurate expression profiling of a moderate number of selected genes, its main advantages being a high sensitivity and specificity, and a broad quantification range. RT-PCR protocols are well known in the art. See for example Derveaux et al. Methods 50 (2010), 227-230. Regardless of the experimental technique employed, appropriate normalization is essential for obtaining an accurate and reliable quantification of gene expression levels. The purpose of normalization is to correct for variability associated with the various steps of the experimental procedure, such as differences in initial sample amount, RNA recovery, RNA integrity, efficiency of cDNA synthesis, and differences in the overall transcriptional activity of the tissues or cells analyzed. Preferably, the PCR analysis also involves detection of one or more tomato housekeeping genes or constitutionally expressed genes such as GAPDH, EFα1, TBP, RPL8, APT, DNAJ, TUA, TIP41, SAND, CAC and SGN-U346908SGN (Exposito-Rodriquez et al. (BMC Plant Biology 2008, 8:131). In addition to detecting the rin gene, the relative expression level of one or more rin target genes may be determined. For example, the rin/rin mutant was found to lack expression of LeACS2, LeACS4, TBG4, LeEXP1, LeMAN4 and PSY1, and shows decreased expression levels of LeACO1, ETR3, PG and INV, while these genes are highly upregulated in the wild-type fruit, indicating that all of these genes are regulated directly or indirectly by rin (Fujisawa et al., BMC Plant Biology 2011, 11:26). Hence, in one embodiment, the invention provides a tomato plant, fruit, fragment or extract thereof for use in a method for inhibiting, preventing or ameliorating disease conditions associated with adipogenesis in a mammal, wherein the tomato lacks expression of LeACS2, LeACS4, TBG4, LeEXP1, LeMAN4 and/or PSY1, and/or shows a decreased expression levels of LeACO1, ETR3, PG and/or INV. Preferably, the expression levels of LeACS2, LeACS4, TBG4, LeEXP1, LeMAN4, PSY1, LeACO1, ETR3, PG and/or INV corresponds to that what is found in a rin tomato.

The expression level can suitably be expressed as relative expression compared to gene-specific expression of the 18S signal. In one embodiment, reduced relative expression of target gene TDR-4 which is associated with the fruit ripening process, is used.

In one embodiment, the tomato has a rin content of at least 53%, like at least 60%, preferably at least 65%, more preferably at least 70%. Very good results are obtained with tomatoes having a rin content of 75-100%.

In a specific aspect, the tomato is selected from the group consisting of the varieties "Slimmy" (rin content 53%), "Mr. Slimmy" (rin content 53%), "Gusto Delight" (rin content 75%), "Snoepboompje" (rin content 75%) and "Tomango" (rin content 100%).

Prior to the present invention, homozygous rin tomatoes (rin/rin) were primarily used for crossing the rin gene in uniformly ripening (u/u) varieties to develop heterozygous (u/rin) tomatoes having a long shelf life (slow ripening). In normal plant breeding, the rin content obtained is generally up to 50% since the crossing of two rin/rin parental lines yields fruits that do not fully ripen and hence cannot be used in conventional tomato breeding programs. The present inventors, recognizing the importance of a high rin content for achieving an anti-adipogenic effect, circumvented this issue by selecting F2 or F3 plants which are strongly heterozygous for rin, and using meristem culturing to obtain identical plants having a rin content of above 50%, like at least 53%, in particular 60-100%.

A ripening-impaired mutant tomato for use in the present invention can be obtained using standard plant technology, in particular plant tissue culturing. In one embodiment, it involves meristem culture which is particularly suitable to store genetic resources of seed producing plants of heterozygous nature. A meristem is a group of undifferentiated plant cells (found at growth tips) which can undergo divisions to form all types of tissues. Generally, the explant used is a shiny dome shaped structure of length less than 0.1 mm with one or two pairs of youngest leaf primordia. Meristematic tissue are isolated and cultivated on a suitable growth medium under aseptic conditions. Meristem forms callus at its cut end on which a large number of shoot primordia develop. These primordia develop into multiple shoots, which after rooting produce small plants bearing 5 or 6 leaves. The shoots grow out directly form excised shoot tip cultured. In shoot tip culture the explant used is meristem along with primordial and developing leaves and adjacent stem tissues.

The invention can be practised using a ripening-impaired mutant tomato, e.g. a rin tomato, plant, fruit, fragment or extract thereof. As used herein, "fragment" refers to a subsection of the plant, like a leave, stem, root, or of the fruit. In one embodiment, the root or fruit is used. Preferably, the fruit or a fruit extract is used. It was found that the anti-adipogenic effect is not restricted to the peel of the fruit but also resides in the pericarp. Hence, whole tomatoes or only pericarp may be used. For the ease of consumption and customer acceptance and appreciation, the use of whole tomato fruits is particularly preferred. For example, it is envisaged that the anti-obese rin tomato is consumed as part of the normal human diet, e.g. as fresh fruits or a processed product thereof like a paste or sauce, thus replacing the traditional tomato with the benefit of reducing fat accumulation.

The mutant tomato can vary in size, from tomberries, about 5 mm in diameter, through cherry tomatoes, about the same 1-2 centimeters (0.4-0.8 inches) size as the wild tomato, up to beefsteak tomatoes 10 centimeters (4 in) or more in diameter. The most widely grown commercial tomatoes tend to be in the 5-6 centimeters (2.0-2.4 in) diameter range. Tomatoes grown for canning and sauces are often elongated, 7-9 centimeters (3-4 in) long and 4-5 centimeters (1.6-2.0 in) diameter; they are known as plum tomatoes, and have a lower water content.

In one embodiment, the invention provides a ripening-impaired mutant tomato extract, paste, sauce or juice, as well as the use thereof to reduce the formation of new adipose tissue and formation of fat reserves in a mammal, in particular to support weight management, promote weight loss and/or to treat obesity. The tomato extract can be obtained by, for example, extracting raw material tomatoes with a suitable solvent. In another embodiment, the tomato fruit is used as a paste or in a dried form.

The raw material tomato to be extracted may be the whole tomato plant, as well as the fruit, pericarp, juice or any other arbitrary parts. A particularly preferred part is the pericarp because it contains a large amount of components having an anti-adipogenic activity (hereinafter referred to as "anti-adipogenic activity components"). In addition, the raw material tomato may also be residues obtained after squeezing the tomato fruit. The squeezed residues are particularly preferred since it contains a large amount of pericarp. Another particularly preferred part is the root because it has a relatively neutral taste and contains, as a powder, fewer hygroscopic components as compared to a powdered fruit.

In one embodiment, the invention provides a tomato plant root or extract thereof for use in a method for inhibiting, preventing or ameliorating disease conditions associated with adipogenesis in a mammal, wherein the tomato is a ripening-impaired mutant, preferably a ripening inhibitor (rin) mutant tomato.

In case that the raw material tomato contains a large amount of moisture, it is preferably used after drying in order to improve efficiency. More specifically, the moisture content is preferably reduced by, for example, drying either naturally or with hot air for 1 to 24 hours at 50 to 150° C. Good results are obtained when raw material is freeze-dried prior to extraction. In addition, in order to increase extraction efficiency, the raw material tomato is preferably used after being finely ground. There are no particular restrictions on the grinding means, and examples of such include a method using a mortar, and methods using a crushing machine such as a whirling blender or a homogenizer. The raw material tomato is preferably ground to a size of 16 mesh or finer.

Raw material tomatoes suitable for extracting anti-adipogenic activity components at high concentrations are those obtained by drying the tomato whole fruits, pericarps or squeezed tomato residues followed by crushing them.

There are no particular restrictions on the solvent used for extraction provided it is capable of extracting the anti-adipogenic activity components, and ordinary polar solvents or amphiprotic solvent and so forth may be used. Examples of solvents that can be used include organic solvents, solvents containing organic solvents or mixed solvents of water and organic solvent. Specific examples of organic solvents include low alcohols (specifically, ethanol, methanol, propanol and butanol), ethers (specifically, diethyl ether), halogenated carbons (specifically, chloroform), nitrites (specifically, acetonitrile), esters (specifically, ethyl acetate) and ketones (specifically, acetone) as well as hexane, dimethyl sulfoxide and dimethylformamide. From the viewpoint of working efficiency, ethanol, methanol and ethyl acetate are preferably used as the organic solvents. Two or more types of the organic solvents may be used in combination. In view of extraction efficiency of the anti-adipogenic activity components, low alcohols, specifically ethanol, methanol, propanol and butanol, preferably methanol or ethanol, is particularly preferred for the solvent. Although there are no particular restrictions on the mixing ratios of water and the organic solvent, the organic solvent is preferably contained in a ratio of 20% or more, and particularly preferably in a ratio of 50 to 99%. Good results were obtained when the solvent is an alcoholic solvent, preferably a methanolic solvent, more preferably MeOH/water in the range of 70:30 to 95:5 (v/v), like 80:20 v.v The invention therefore also relates to a method for producing an anti-adipogenic agent, comprising extracting raw material of a tomato plant, fruit or fragment thereof with a solvent, the tomato being a ripening-impaired mutant tomato, for instance having a rin content of at least 50%. When considering that the tomato extract will ultimately be added to foods or cosmetics and so forth, ethanol is particularly preferable. In this case, in addition to 100% methanol, aqueous alcohol, preferably 40 to 90% methanol solution, and particularly preferably 60 to 90% ethanol solution, can be used.

There are no particular restrictions on the mixing ratios of the raw material tomato and the solvent during extraction, however, the solvent is preferably used in an amount of 2 to 20 times by weight, based on the weight of the raw material tomato, preferably 5-15 times by weight. For example 2-20 ml solvent is used per gram of lyophilized extract of a tomato fruit. When methanol is used as a solvent, the extraction temperature is preferably at around room temperature (18-23° C.), and the extraction time is preferably within the range of 30 minutes to 24 hours. It may be preferred to (partially) perform the extraction process under ultrasonic treatment and/or vigorous shaking.

Furthermore, prior to extraction with a solvent containing the organic solvent, impurities that are soluble in water can be removed by extracting the raw material tomato with cold water or hot water. In this case, the residues are recovered after water extraction and subjected to solvent extraction.

In the process of extraction, anti-adipogenic activity components elute into the solvent. Since the anti-adipogenic activity components are efficiently extracted by organic solvents, and particularly by alcohol-containing solvents, these components are expected to be present in a large amount, particularly in alcohol-soluble components of the tomato.

It is preferable to repeat the extraction step several times in order to improve extraction efficiency. Following extraction, solvent that contains the tomato extract is recovered by performing suction filtration and the like. As a result of the above procedure, a liquid tomato extract may be obtained. Alternatively, the solvent is removed partially or completely (e.g. under vacuum) to obtain a concentrated liquid tomato extract or a dried tomato extract. Furthermore, the resulting fraction may be further purified by a synthetic adsorbent or ion exchange resin, etc. as necessary.

To determine anti-adipogenic activity of the dried extract, it is suitably dissolved in a small volume of a suitable solvent, like DMSO. The resulting tomato extract can be used as an anti-adipogenic agent, regardless of its state, whether it is in a state which contains a solvent or it is concentrated, or it is a dried product in which solvent has been removed from the extract. However, in view of storage properties and safety of the organic solvent, the tomato extract is preferably obtained in a dried state. The anti-adipogenic agent of the present invention can be characterized by comprising ripening-impaired mutant tomato fruit, root, part or extract thereof as an active ingredient.

Thus, also provided herein is an anti-adipogenic agent comprising an extract of a tomato plant, fruit or fragment thereof as an active ingredient, wherein the tomato is a ripening-impaired mutant tomato. The tomato plant, fruit, fragment or extract thereof is suitably obtained from a mutant tomato carrying the rin, nor and/or Nr gene. For example, the tomato is heterozygous or homozygous for rin, nor and/or Nr. In one embodiment, the tomato has a rin, nor and/or Nr content of at least 53%, preferably at least 65%, more preferably 70-100%. In one specific embodiment, the tomato has a rin content of at least 53%, preferably at least 65%, more preferably 70-100%. Preferably, the tomato is a rin homozygote.

The use of fruits and/or roots are particularly preferred for extraction. The extract can be a liquid or a dry extract. The extract may contain one or more additives or auxiliary components, which may be used to improve the colour, odour, appearance, flavour, texture and/or storage stability. Exemplary components include fillers, preservatives, antioxidants, flavourings, sweeteners and acidity regulators.

In one embodiment, the extract is an alcoholic extract, preferably a methanolic extract, more preferably an extract prepared by MeOH/water in the range of 70:30 to 95:5 (v/v), more preferably 80:20 (v/v). The anti-adipogenic agent is capable of inhibiting insulin-induced adipogenesis in cultured murine 3T3 fibroblasts. Preferably, in vitro adipogenesis induced by a 10-day treatment with 10 µg/ml insulin is inhibited by the agent or reconstituted agent or dilution thereof (e.g. 1:1000 to 1:20.0000 in DMSO) with at least 30%, preferably at least 40%. Preferably, adipogenesis is determined by staining for lipid droplets, for instance using Oil Red O.

The invention also provides the use of a ripening-impaired mutant tomato, preferably a rin tomato, plant, fruit, fragment or extract thereof in a method for preventing weight gain, and/or treating an obesity-related condition in a mammal. In one embodiment, the use comprises inhibiting, preventing or ameliorating a disease condition associated with adipogenesis, wherein the mammal is human or an animal. Preferably, the human or animal is overweight or obese. Obesity in pets is common in many countries. Rates of overweight and obesity in dogs in the United States ranges from 23% to 41% with about 5.1% obese. Rates of obesity in cats were slightly higher at 6.4%. In Australia, the rate of obesity among dogs in a veterinary setting has been found to be 7.6%. Thus, veterinary applications of the mutant tomato are also envisaged. Tomato extracts are particularly preferred for veterinary applications since these can be easily incorporated in the diet. In one aspect, the mammal is a house-hold pet like a cat or a dog.

Preferably however, the mammal is a human individual, in particular a human individual that is at increased risk to gain weight and/or to acquire an obesity-related condition, in particular a disease condition associated with adipogenesis. For example, the human individual suffers from or is predisposed to develop obesity, lipid storage disease, hyperlipemia, type 2 diabetes, heart disease, stroke, hypertension, cancer, metabolic syndrome, gallbladder disease, gout, sleep apnoea, asthma or childhood obesity. In one embodiment, the human is at least 16 years old and preferably an adult.

Also provided is a method for inducing weight loss and/or preventing weight gain in a subject comprising administering to the subject a therapeutically effective amount of a pharmaceutical formulation comprising a ripening-impaired tomato plant, fruit, fragment or extract thereof, and a pharmaceutically acceptable carrier. The subject is preferably a human subject. The formulation is preferably administered to the subject 1-4 times daily. The formulation is typically administered for at least 2 weeks, preferable at least one month.

According to the invention the tomato fruits or extracts thereof may be offered as food supplement, functional food ingredients or as pharmaceutical ingredients in order to prepare a composition for oral administration for preventing and/or treating an obesity-related condition in a mammal. A still further aspect of the invention therefore relates to a pharmaceutical or neutraceutical, composition comprising a tomato plant, fruit, fragment or extract thereof, wherein the tomato is a ripening-impaired mutant tomato. Preferably, the composition comprises a ripening-impaired mutant tomato fruit or root extract. In a preferred embodiment, the tomato is a rin mutant tomato. For example, the composition comprises heterozygous or homozygous rin tomato fruit, root or an (alcohol) extract thereof. Preferably, the rin content is at least 65%, preferably 70-100%. For example, the tomato is selected from the group consisting of the varieties "Slimmy", "Mr Tasty", "Gusto Delight" and "Tomango".

The amount of a tomato plant, fruit, fragment or extract thereof can vary according to specific needs or desired effects. It was found that the daily intake of about 1-4 medium sized tomatoes (i.e. about 20-100 grams) of a rin homozygote was sufficient to exert an adipogenic effect in a human being of approximately 70 kgs. Hence, in one embodiment the composition comprises the equivalent of at least 0.25 gram, preferably at least 0.5, more preferably at least 1 gram of tomato fruit per kg bodyweight if the composition is in the form for daily dosage or consumption. Of course, the equivalent amount can be adapted accordingly where a less or a more frequent dosage is intended. The equivalent amount can of course also be present in the form of an extract, preferably an alcoholic extract.

In one embodiment, the composition is intended for use in humans, e.g. as part or in support of an anti-adipogenic diet. The composition preferably comprises one or more further beneficial ingredients. Preferably, it comprises probiotics and/or prebiotics, preferably dietary fibres.

It has been shown that gut microbiota plays an intricate role in the regulation of body weight (P. J. Turnbaugh, F. Backhed, L. Fulton, J. I. Gordon, Cell Host Microbe 3, 213(2008). Transplantation experiments of the microbiota from obese and lean mice into microbe-free mice also proved that the compositional change of microbiota in the gastrointestinal (GI) tract resulted in differences in the efficiency of caloric extraction from food, eventually contributing to differential body weights. These results suggest that small changes in caloric extraction in the GI tract by xenobiotically manipulated intestinal bacteria can lead to a meaningful reduction in body weight. Accordingly, in one embodiment the invention provides a composition comprising a tomato plant, fruit, fragment or extract thereof, wherein the tomato is a ripening-impaired mutant tomato, and at least one probiotic capable of promoting weight loss in a mammal. In one embodiment, the probiotic is a *Lactobacillus*, e.g. selected from the group consisting of *Lactobacillus acidophilus* FARM1 KCTC 11513BP, *Lactobacillus acidophilus* FARM2 KCTC 11514BP and *Lactobacillus acidophilus* FARM3 KCTC 11515BP, *Lactobacillus helveticus* CNCM 1-4095 *Lactobacillus rhamnosus* CNCM 1-4096 and *Lactobacillus gasseri* SBT2055 (LG2055).

Alternatively, or additionally, the composition can contain a prebiotic, like dietary fibres. Dietary fibres are an important part of a healthy and balanced nutrition and are important for its role in the health of the colon and the small intestine cells, i.e. colonocytes and enterocytes. Dietary fibres may prevent damage of them. Dietary fibres are generally regarded as the indigestible portion of plant or vegetable foods. They are carbohydrates, more specifically non-starch poly- and oligosaccharides, and lignin, primarily derived from plant cell walls that cannot be hydrolyzed by human digestive enzymes. However, they often can be fermented by intestinal bacteria to produce hydrogen, methane, carbon dioxide, water and short chain fatty acids (SCFA). Its function differs in the small and large intestine. Its primary function in the small intestine is to enhance viscosity, while in the large intestine, it is to serve as a substrate for the gut flora in order to produce the short chain fatty acids.

In this invention soluble dietary fibres are, preferably, used as well in form of large chains, i.e. polysaccharides, as in form of short chains, i.e. oligosaccharides. When soluble fibres are consumed, the undigested portion serves as substrate for the gut flora. Depending on the type of soluble fibre, different bacterial groups are stimulated. Therefore the present invention proposes to use preferential at least two types of fibre in order to obtain an optimal result. Several clinical studies have shown that administering oligosaccharides such as fructo-oligosaccharides (FOS), galacto-oligosaccharides (GOS or GaOS), gluco-oligosaccharides (GOS or GluOS) or xylo-oligosaccharides (XOS) can increase the number of friendly or beneficial bacteria while reducing the population of harmful bacteria. Several dietary fibres, such as the oligosaccharides discussed, have also been defined as prebiotics. For a food ingredient to be classified as a prebiotic it must fulfil the following criteria: (i) neither be hydrolysed, nor absorbed in the upper gastrointestinal tract, (ii) be selectively fermented by one or a limited number of bacteria potentially beneficial to the colon, and (Hi) be able to alter the colonic micro flora towards a healthier composition, by increasing friendly bacteria and reducing harmful or putrefactive bacteria. Since dietary fibres provide such a broad range of nutritional and health benefits, they are added to many food products and are provided as separate food supplements or prebiotic compositions.

For example the composition is an edible tomato-based food product comprising processed ripening-impaired mutant tomato fruits and at least one prebiotic and/or at least one probiotic. Exemplary food products include tomato juice, tomato ketchup, dried tomatoes, pickled tomatoes, tomato paste, pureed tomato, tomato-based sauces, soups, beverages and tomato-based spreads. Processed tomato products such as tomato juice, pureed tomato, tomato pastes and tomato ketchup are generally being produced by washing tomato fruit, preliminarily heating (primarily for enzyme deactivation) washed tomato fruit, extracting juice from the preliminarily heated washed material, heating (primarily for sterilization) or further condensing and similarly heating such an extracted juice after mixing.

In another embodiment, the invention provides an animal food composition comprising a tomato plant, fruit, fragment or extract thereof, wherein the tomato is ripening-impaired mutant tomato, preferably a ripening inhibitor (rin) mutant tomato. For example, it is a "light" household pet formula suitably used to control the body weight of a pet.

LEGEND TO THE FIGURE

FIG. 1: Inhibition of in vitro adipogenesis by rin tomato extracts using an established murine 3T3-L1 fibroblasts model system. TNFalpha was used as positive control to inhibit insulin-induced fat accumulation. Negative control: insulin-induced cells. Solvent control:insulin-induced cells with 0.1% DMSO. Elegance: insulin-induced cells with extract of control tomato variety 'Elegance' 0% rin. Gusto Delight: insulin-induced cells with extract of rin tomato variety 'Gusto Delight' (75% rin). Tomango: insulin-induced cells with extract of rin tomato variety 'Tomango' (rin homozygote; 100% rin).

EXPERIMENTAL SECTION

Determination of Rin Content

Using an RNeasy Plus Mini Kit (Qiagen, Hilden, Germany), total RNA was extracted and purified from tomato fruits of varieties having different rin contents, including a normal (a genotype of RIN/RIN) plant, (mature green, pink coloring and red ripe) and of a rin mutant (rin/rin) plant at periods corresponding to these stages, as previously described (Kitagawa et al., Characterization of tomato fruit ripening and analysis of gen expression in F1—Hybrids of the ripening inhibitor (rin) Mutant. Physiol Plantarium 2005, 123 (3):331-338). Complementary DNA was synthesized from total RNA using a PrimeScript II first cDNA strand synthesis kit (Takara Biotech) and then applied in real-time PCR as a template. Expression levels of the rin genes were analyzed by quantitative real-time reverse transcription PCR (qRT-PCR) using oligonucleotide primers specific for rin (GenBank accession number AF448522).

Preparation of Tomato Extract

Fresh tomato fruits were cut into pieces of about 1×1×1 cm. Whole fruits were used. Following freeze-drying of the pieces, the freeze dried material was ground into a homogenous powder using a pestle and mortar. The powder was extracted with extraction solvent (methanol or a methanol/water 80:20 v/v/mixture). Typically, 13 mL solvent was used to extract 1 gram powder. Extraction was performed at room temperature (30 min ultrasound followed by 30 min vigorous shaking). The extraction mixture was centrifuged and the supernatant dried under vacuum. The dried extract was redissolved in DMSO (Q:volume?) prior to use in adipogenesis assays. The concentration of the extract corresponds to 375 mg/ml of the original powder.

In Vitro Adipogenesis Assay

The assay was performed according the protocol previously described by Niwano et al. (Niwano et al. Extensive screening for plant foodstuffs in Okinawa, Japan with anti-obese activity on adipocytes in vitro. Plant Foods Hum Nutr. 2009 March; 64(1):6-10).

The final concentration of the tomato extracts present in the assay was 1:10.000 compared to the DMSO extract (i.e. corresponding to 37.5 μg of the original powder per ml. The final DMSO concentration was 0.1%. TNFα (10 ng/ml) was used as positive control to inhibit adipogenesis.

Murine 3T3-L1 fibroblasts (Dainippon Pharma Co., Ltd., Osaka, Japan) were adjusted to be 30,000 cells/ml in DMEM supplemented with 10% CS, and 200 μl of the cell suspension were planted into 96-well culture plate and incubated at 37° C. in a humidified 5% $CO_2$ incubator for 2 days. The medium was changed to DMEM supplemented with 10% FCS, 0.5 mM IBMX and 1 μM DEX, and further incubated for 2 days (initiation of differentiation). The medium was changed to DMEM supplemented with 10% FCS and 10 μg/ml of insulin, and was further incubated for 2 days. Thereafter, the medium was changed to normal culture medium (DMEM supplemented with 10% FCS), and was freshly replaced every 24 h. Each sample solution (tomato extract or control) was added from the initiation of differentiation (day 0) to day 10.

The invention claimed is:

1. A method for preventing weight gain, inhibiting, preventing or ameliorating a disease condition associated with adipogenesis in a mammal, wherein the method comprises the step of:
   administering to the mammal an extract of pericarp or root of a ripening-impaired mutant tomato having a rin, nor, or Nr content of at least 50 percent, wherein the extract is an anti-adipogenic agent, wherein the extract further comprises a prebiotic.

2. The method according to claim 1, wherein the tomato carries the rin gene, wherein the rin content is at least 70 percent.

3. The method according to claim 2, wherein the tomato is a rin homozygote.

4. The method according to claim 1, wherein the extract is prepared by alcoholic extraction.

5. The method according to claim 1, wherein the mammal is a human individual, wherein the extract is prepared with at least 0.25 gram of the pericarp or root per kilogram of bodyweight of the human, wherein the method further comprises the step of:
   administering the extract between one to four times per day, wherein the extract is administered for at least two weeks.

6. A method for preventing weight gain, inhibiting, preventing or ameliorating a disease condition associated with adipogenesis in a mammal, wherein the method comprises the steps of:
   freeze-drying or spray-drying raw material of pericarp or root of a ripening-impaired mutant tomato having a rin, nor, or Nr content of at least 50 percent;
   extracting the raw material of pericarp or root with a solvent, wherein the solvent is MeOH/water in the range of 70:30 to 95:5 (v/v) thereby creating an extract; and administering to the mammal a therapeutically effective amount of the extract and a pharmaceutically acceptable carrier, wherein the extract is an anti-adipogenic agent.

7. A method for preventing weight gain, inhibiting, preventing or ameliorating a disease condition associated with adipogenesis in a mammal, wherein the method comprises the steps of:
   extracting raw material of pericarp or root of a ripening-impaired mutant tomato having a rin, nor, or Nr content of at least 50 percent with a solvent, wherein the solvent is a mixture of water and alcohol, thereby creating an extract; and
   administering to the mammal a therapeutically effective amount of the extract and a pharmaceutically acceptable carrier, wherein the extract is an anti-adipogenic agent.

8. The method according to claim 7, wherein the alcohol is ethanol, methanol, propanol, or butanol.

9. The method according to claim 7, wherein the solvent is 50 to 99% (v/v) alcohol in water.

10. The method according to claim 7, wherein the extract further comprises a prebiotic.

11. The method according to claim 7, wherein the tomato carries the rin gene, wherein the rin content is at least 70 percent.

12. The method according to claim 11, wherein the tomato is a rin homozygote.

13. The method according to claim 11, wherein the tomato is selected from the group consisting of the varieties Slimmy, Mr. Tasty, Gusto Delight, and Tomango.

14. The method according to claim 10, wherein the prebiotic is at least two of the group consisting of fructo-oligosaccharides, galacto-oligosaccharides, and xylo-oligosaccharides.

15. The method according to claim 7, wherein the mammal is a human individual, wherein the extract is prepared with at least 0.25 gram of the pericarp or root per kilogram of bodyweight of the human, wherein the method further comprises the step of:
    administering the extract between one to four times per day, wherein the extract is administered for at least two weeks.

16. The method according to claim 15, wherein the human individual suffers from, or is predisposed to develop, obesity, lipid storage disease, hyperlipemia, Type 2 diabetes, heart disease, stroke, hypertension, cancer, metabolic syndrome, gallbladder disease, gout, sleep apnea, asthma, or childhood obesity.

17. The method according to claim 10, wherein the tomato carries the rin gene, wherein the rin content is at least 70 percent.

18. The method according to claim 17, wherein the tomato is selected from the group consisting of the varieties Slimmy, Mr. Tasty, Gusto Delight, and Tomango.

19. The method according to claim 18, wherein the prebiotic is at least two of the group consisting of fructo-oligosaccharides, galacto-oligosaccharides, and xylo-oligosaccharides.

20. The method according to claim 19, wherein the mammal is a human individual, wherein the extract is prepared with at least 0.25 gram of the pericarp or root per kilogram of bodyweight of the human, wherein the method further comprises the step of:
    administering the extract between one to four times per day, wherein the extract is administered for at least two weeks.

* * * * *